United States Patent [19]

Putz

[11] Patent Number: 4,869,255
[45] Date of Patent: Sep. 26, 1989

[54] ELECTRICAL CONNECTION DEVICE

[75] Inventor: David A. Putz, Racine, Wis.

[73] Assignee: Ad-Tech Medical Instrument Corp., Racine, Wis.

[21] Appl. No.: 218,161

[22] Filed: Jul. 13, 1988

Related U.S. Application Data

[63] Continuation-in-part of Ser. No. 128,797, Dec. 4, 1987, which is a continuation-in-part of Ser. No. 109,111, Oct. 16, 1987, abandoned.

[51] Int. Cl.$^4$ .............................................. A61B 5/04
[52] U.S. Cl. .................................... 128/642; 439/692; 439/790; 439/909
[58] Field of Search ............... 128/642, 644, 784–786, 128/798, 799, 419 P, 804; 439/692, 790, 796, 909

[56] References Cited

U.S. PATENT DOCUMENTS

| | | | |
|---|---|---|---|
| 3,866,615 | 2/1975 | Hewson | 128/784 X |
| 4,245,645 | 1/1981 | Arseneault et al. | 128/642 |
| 4,516,820 | 5/1985 | Kjzma | 128/784 X |
| 4,633,889 | 1/1987 | Talalla et al. | 128/784 |
| 4,676,258 | 6/1987 | Inokuchi et al. | 128/804 |
| 4,712,557 | 12/1987 | Harris | 128/419 P |

Primary Examiner—Lee S. Cohen
Attorney, Agent, or Firm—Peter N. Jansson, Ltd.

[57] ABSTRACT

An electrical brain-contact device and device for connecting a plurality of lead wires with individual conductors. The lead wires extend to a terminal mount and to an array of terminals; a conductor support holds an array of the individual conductors; and a connector block with a first space and an array of second spaces serves to join the conductors to the terminals, preferably by a biasing means. The first space receives the terminal mount and the array of second spaces receives the conductor array. The block may be single or have a plurality of sub-blocks attached end-to-end allowing the block to be sized to accept any number of terminals and conductors. Each block or sub-block is preferably a non-conductive one-piece member.

24 Claims, 3 Drawing Sheets

ELECTRICAL CONNECTION DEVICE

RELATED APPLICATIONS

This is a continuation-in-part of patent application Ser. No. 128,797, filed Dec. 4, 1987, entitled IMPROVED ELECTRICAL BRAIN-CONTACT DEVICES, which in turn is a continuation-in-part of patent application Ser. No. 109,111, now abandoned, filed on Oct. 16, 1987, entitled IMPROVED ELECTRICAL BRAIN-CONTACT DEVICES, now abandoned.

FIELD OF THE INVENTION

This invention is related generally to electrical connection devices for wire having multiple independent conductive lines and, in particular, to connectors for rapid connection and disconnection. More specifically, this invention is related to multi-electrode brain-contact devices and means on such devices for facilitating surgical procedures for their placement and set-up, including their electrical connection at a position away from the brain.

BACKGROUND OF THE INVENTION

Accurate sensing of intracranial electrical activity, for the purpose of determining epileptogenic foci or otherwise, typically requires use of a plurality of brain contacts. Epileptogenic mapping is one example of the use of electrical devices with plural-contact tissue-engagement members. Broadly speaking, there are two different kinds of intracranial electrical contact devices—depth probes and flexible flat surface members.

Depth probes, which are often referred to as "depth electrodes," penetrate deep into the brain tissue. On the other hand, flexible flat surface members, including what are sometimes referred to as "strip" electrodes and "grid" electrodes, are placed subdurally in direct contact with brain tissue at the surface of the brain.

Each of these different kinds of intracranial tissue-engagement members has a plurality of electrodes which are separated from one another by a non-conductive material on which the electrodes are mounted. Separate thin insulated lead wires extend from the tissue-engagement member for each electrode. Such lead wires extend away from the tissue-engagement member to means for connecting the lead wires with individual conductors, which lead to monitoring or recording equipment.

For each type of intracranial tissue-engagement member used in the prior art, the procedures for placement and hookup are of great importance. It is essential that the tissue-engagement members be inserted with a high degree of accuracy in order to avoid damage and in order that placement be in the most advantageous positions. It is also important that the flat flexible member be in proper contact with brain tissue for advantageous results. It is also essential that the lead wires extending from the tissue-engagement member be properly connected and that the fragile lead wires remain functional, without any breakage or disconnection.

While there has been much progress in the field of electrical brain-contact devices in recent years, existing devices and procedures have a number of problems and drawbacks. One significant problem is that the surgical placement and set-up procedures preceding the period of use are far too time-consuming and complex. Such procedures in some cases also lead to specific problems.

Such problems can be described best by generally describing at least certain parts of the placement and set-up procedures, as used, for example, in preparing for an extended period of epileptogenic sensing using grid or strip electrodes as the tissue-engagement members:

One of the early steps in existing placement and set-up procedures for grid and strip electrodes is making an incision in t he scalp over the site of proposed electrode placement. Then a burr hole is drilled in the skull or a skull area otherwise removed. One or more incisions are then made in the dura to accommodate placement of a grid or insertion of a strip. Dural tack-up sutures are placed in both dural margins.

The grid or strip electrode device is then placed or inserted, with the electrodes in contact with the brain tissue. When strip electrodes are used, a plurality of strips are usually inserted in each burr hole. The strips and grids may have a large number of electrical contacts. With grid electrodes, the number of contacts may be particularly high. After the grid or strips have been positioned, the dural edges are approximated with a suture.

The lead wires, which extend from the proximal end of each strip or grid, are passed through the sutured dura incision. All the wires, one for each electrode on the grid or on every strip, are then brought out through the skin by passing them through a needle and then drawing them through the scalp at a distance (usually 4–5 cm) from the skull opening. When there are numerous wires it is often necessary to tunnel in a number of directions through the scalp to sites spaced from the skull opening. This can be both very time-consuming and very hard on the patient's head.

When such wires have exited the scalp at the chosen sites, it then remains necessary to make electrical hookups of each of such wires in the appropriate manner. This is itself a time-consuming operation, and one in which there is a risk of incorrect hookups. The extended time required for such hookups is a problem in itself. And, the fragile lead wires are quite susceptible to breakage during these manipulative operations; if this occurs, it may be necessary to reopen the dura to remove and replace the grid or strip from which the lead wire broke and repeat many of the procedures described above.

In order to minimize the likelihood of lead wire breakage, lead wires of greater size may be used. However, increasing the diameter of the lead wires tends to increase the overall thickness of the strip or grid. Thickness can be undesirable in such flat flexible members and can in some cases pose problems for the electrical sensing operations. Increasing wire thickness can increase the cost of the device, particularly if silver or platinum wire is used.

When the tissue-engagement member is a depth electrode device, some of the problems may vary to some extent. However, the problems of time-consuming electrical hookup procedures are quite similar. Indeed, such problems are involved with electrical hookup of any plural-contact tissue-engagement member.

There is a substantial need for an improved plural-contact electrical connection device overcoming or minimizing the above problems and difficulties. In particular, there is a need for improved electrical hookup apparatus for use during placement and setup procedures involving electrical contact with brain tissue. A simple plural-contact connector which is easily usable and disposable would be highly desirable.

OBJECTS OF THE INVENTION

It is an object of this invention to provide an improved electrical connector for brain-contact devices overcoming certain problems of the prior art, including those mentioned above.

Another object of this invention is to provide an improved electrical brain-contact device which facilitates surgical procedures used in locating epileptogenic foci.

Another object of this invention is to provide an improved electrical brain-contact device which may be electrically connected easily and quickly during surgical placement and set-up procedures.

Another object of this invention is to provide an electrical connector which reduces or eliminates breakage of lead wires during insertion of brain-contact devices.

Another object of this invention is to provide an improved electrical connection device which provides rapid and accurate electrical hookup of large numbers of electrodes and lead wires during surgical procedures.

Another object of this invention is to provide an improved electrical brain-contact device allowing the use of lead wires of substantially reduced diameter.

It is an object of this invention to provide an improved electrical connector for use in connecting a plurality of lead wires with individual conductors.

Another object of this invention is to provide an improved electrical connector for plural lead wires which is simple in construction and operation.

These and other important objects will be apparent from the descriptions of this invention which follow.

SUMMARY OF THE INVENTION

The parent applications referred to above describe certain advances which have been made toward avoiding or minimizing the above problems. This invention described herein represents a further improvement, overcoming or minimizing such problems.

The invention is an improvement in electrical devices for brain contact of the type having a tissue-engagement member with a plurality of electrodes, separate lead wires from the tissue-engagement member for each electrode, and means away from the tissue-engagement member to connect the lead wires with individual conductors, such as conductors leading to equipment for recording of electrical impulses. More generally, this invention is an improved electrical connection device of the type for connecting a plurality of lead wires with individual conductors.

In the device of this invention, the lead wires extend to a terminal mount and to an array of lead-wire terminals on and forming a part of the terminal mount. A conductor support holds the individual conductors in a conductor array. A connector block, hereafter described, serves to join the lead-wire terminals to the individual conductors and hold them firmly in engagement.

The connector block has a first space and an array of second spaces each of which intersect the first space. The first space receives the terminal mount and the array of second spaces receives the conductor array. Broadly described, the connector block, terminal mount and conductor array are configured and arranged such that the lead-wire terminals and individual conductors are held in engagement by mechanical interference.

In preferred embodiments of this invention, the terminal mount is an elongate member having the lead-wire terminals spaced therealong. For example, the terminal mount may include a tubular sheathing covering all the lead wires and rings around and spaced along the sheathing forming the lead-wire terminals. In such cases, the first space in the connector block may be a first elongate cavity in the connector block formed of non-conductive material and shaped to receive the elongate member.

In such preferred embodiment, the individual conductors are preferably male members which protrude from the conductor support. The second spaces are preferably second elongate cavities in the conductor block formed of non-conductive material and shaped to receive the male members.

Preferred embodiments of this invention include means biasing the male members and lead-wire terminals together at the intersections of the second elongate cavities with the first elongate cavity. In one form of such preferred embodiment, the lead-wire terminals have substantially fixed cross-dimensions, the connector block has a pair of adjacent second elongate cavities corresponding to each lead-wire terminal, and each individual conductor includes a pair of said male members which enter the pair of second elongate cavities and spread slightly to receive a lead-wire terminal.

The male members of each pair of male members are spaced from each each other by a distance less than the fixed cross-dimension of the corresponding lead-wire terminal. This dimensioning requires forcible spreading of the male members of each pair for engagement with the corresponding lead-wire terminal. The forcible spreading provides the biasing means for reliable electrical contact and mechanical engagement.

The connector block is preferably substantially transparent. This may be accomplished by molding or machining the connector block of a tough substantially transparent plastic material. Using such materials, allows viewing of the engagement of the conductors with the lead-wire terminals, which provides assurance of proper connection. The connector block is preferably integrally formed of just one material. Each block is preferably of non-conductive one-piece construction.

The connector block of this invention preferably includes a main surface which extends substantially parallel to the first elongate cavity, with the second elongate cavities each extending from such main surface to intersection with the first elongate cavity. The connector block may be a single block with any number of second elongate cavities. Or, the connector block may be formed of a plurality of sub-blocks which are attached end-to-end by mating means on each adjacent pair of sub-blocks.

In the case of plural sub-blocks, each sub-block forms a portion of the first elongate cavity and a portion of the main surface. And each sub-block has a subset of the second elongate cavities. Thus, the connector block can be sized to accommodate varying numbers of lead-wire terminals and conductors by choosing the number of sub-blocks to be attached to one another.

The mating means which join the sub-blocks preferably have stop means facilitating co-alignment of the first elongate cavity portions and co-alignment of the main surface portions. The mating means holding the sub-blocks together are preferably corresponding male and female dove-tail connectors, and the stop means used for alignment purposes may be the ends of the female and male elements.

In certain preferred embodiments, the main surface of the connector block includes an off-center recess (hole) on it which serves to dictate the orientation of the conductor support with respect to it when the conductors extending therefrom are engaged in the second elongate cavities. A guide pin, which extends from the conductor support along with the male conductor members, is received in the off-center recess only when the conductor support is in the proper orientation. This serves as a further means to assure accurate connection of the conductor members to the lead-wire terminals.

In some preferred embodiments, the connector block has opposed finger-grip protrusions along its opposed sidewalls. Such protrusions serve to facilitate detachment of the connector block from the conductor support, and, when a sub-block construction is used, to aid in detachment of the sub-blocks from one another.

DETAILED DESCRIPTIONS OF PREFERRED EMBODIMENTS

Figure 5:
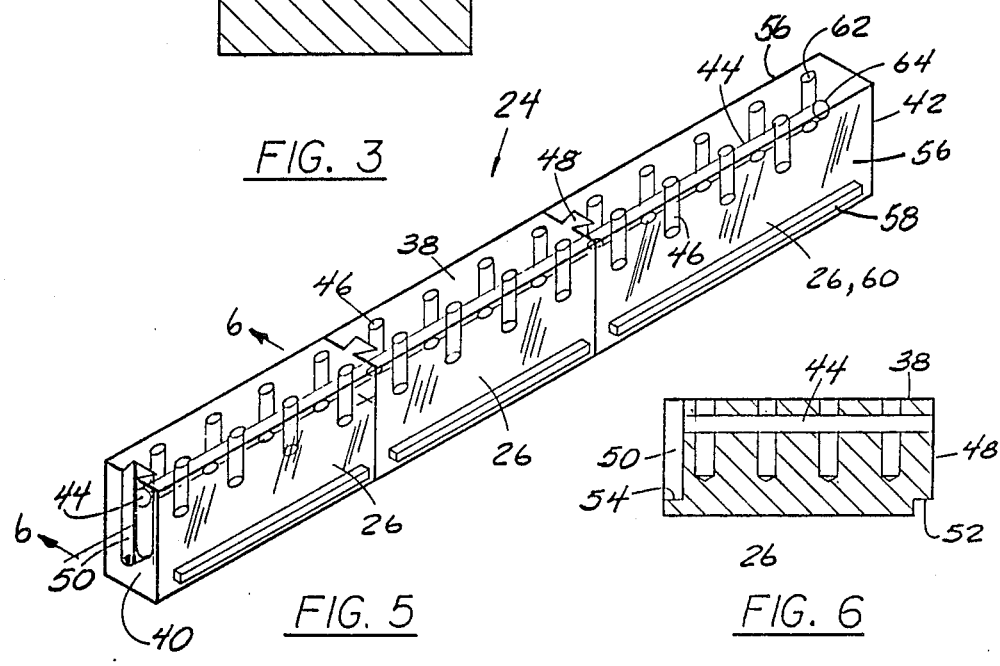
FIG. 5 is an enlarged perspective view of another embodiment, which has a plurality of sub-blocks.
Figure 6:
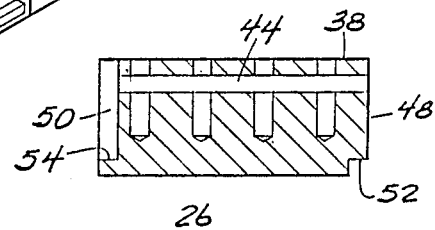
FIG. 6 is a fragmentary side sectional view of the device of FIG. 5, taken along section 6—6 as indicated in FIG. 5.

FIGS. 1-4 illustrate an electrical brain contact device 10 including a tissue-engagement member 12, a tubular sheathing 14 within which lead wires 16 extend toward a terminal mount 18 (see FIG. 2), a conductor support 20, and a single unitary connector block 22. FIGS. 5 and 6 illustrate an alternative connector block 24 formed of a plurality of sub-blocks 26. Like parts are identified by like numerals in the drawings.

Figure 1:
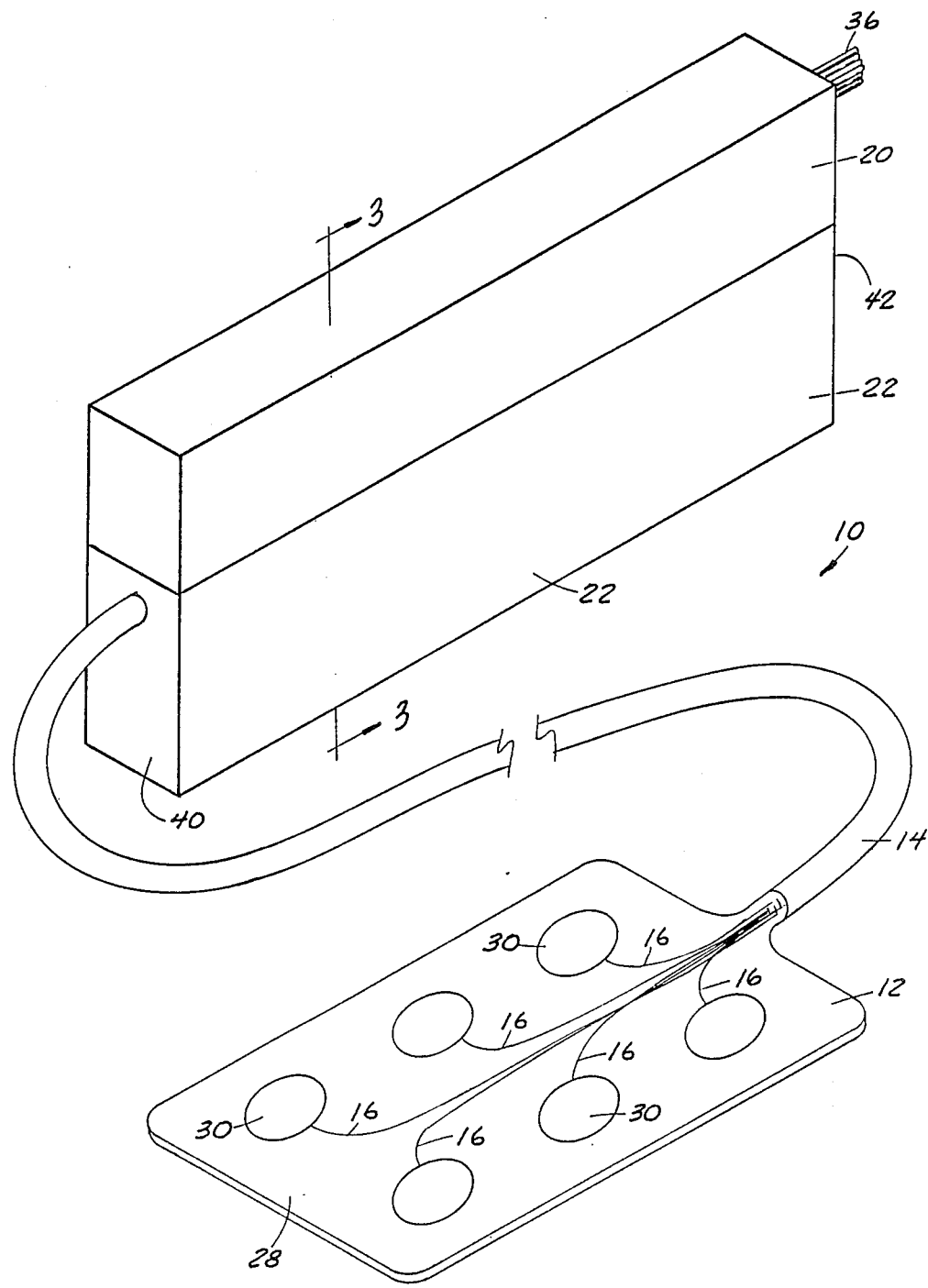
FIG. 1 is an enlarged perspective view of a preferred electrical brain-contact device in accordance with this invention, with its electrical connection device assembled as in use.

Tissue-engagement member 12, shown in FIG. 1, is a "grid electrode" which includes a flexible sheet member 28 and a number of flat electrode disks 30 held by and co-planar with flexible sheet member 28. Sheet member 28 is formed by a pair of flexible sheets with electrode disks 30 between them. Also held between the flexible sheets of sheet member 28 are lead wires 16, one wire attached to each electrode disk 30. Lead wires 16, each of which has its own thin layer of insulation, come together at the edge of flexible sheet member 28 where they enter sheathing 14.

Figure 2:
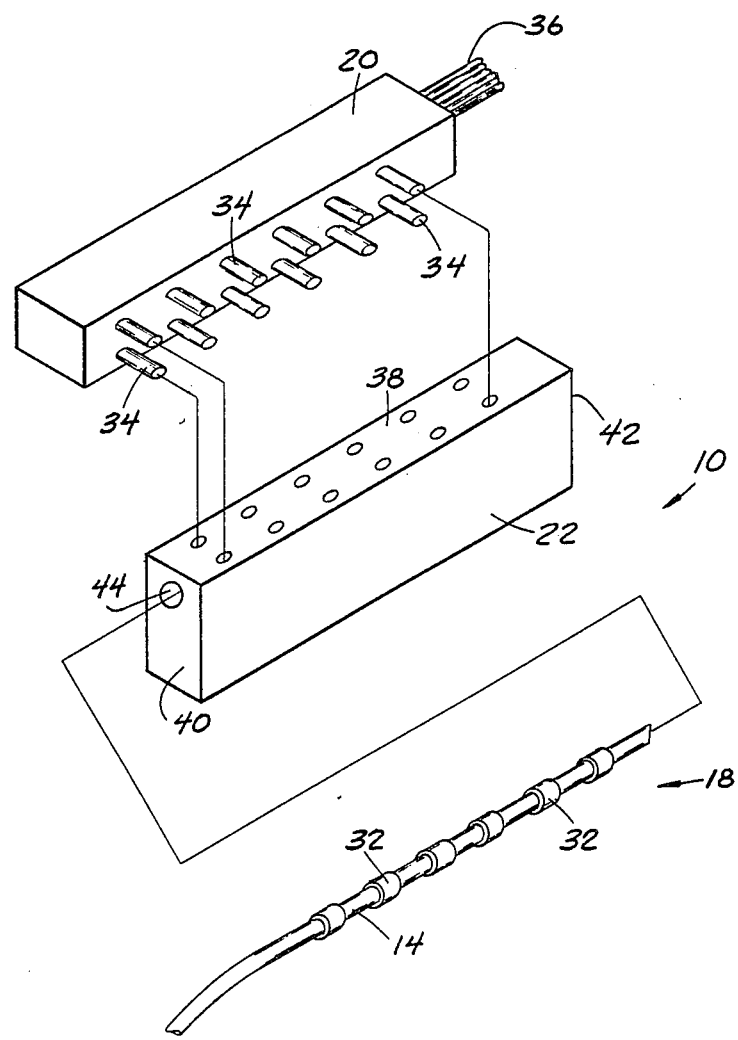
FIG. 2 is a reduced fragmentary perspective view of the device of FIG. 1, showing the electrical connection device in unconnected condition.
Figure 3:
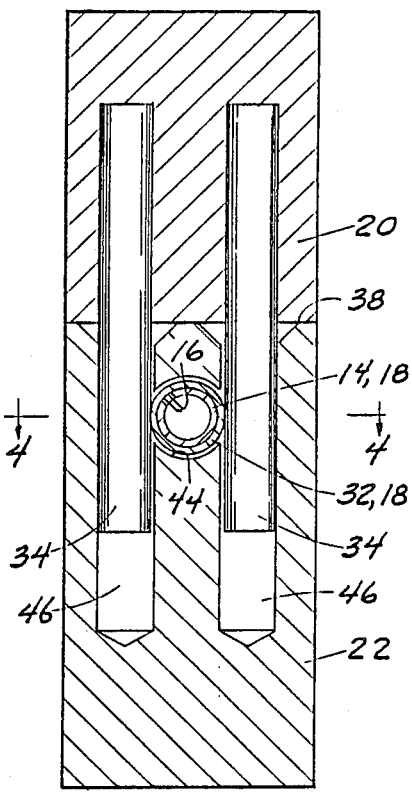
FIG. 3 is an enlarged sectional end view of the device of FIG. 1, taken along section 3—3 as indicated in FIG. 1.
Figure 4:
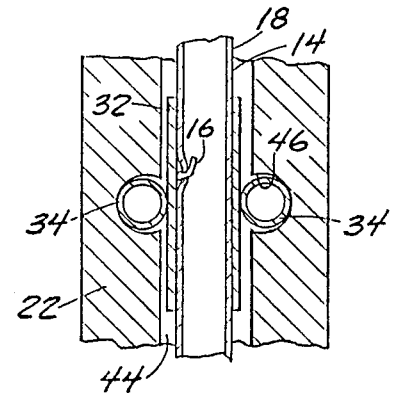
FIG. 4 is a fragmentary top sectional view of the device of FIG. 3, taken along section 4—4 as indicated in FIG. 3.

Lead wires 16 and sheathing 14 over them extend from tissue-engagement member 12 to terminal mount 18, shown best in FIG. 2. Terminal mount 18 is an elongate member. Sheathing 14 extends into and becomes part of terminal mount 18, forming a base for mounting of lead-wire terminal rings 32. Each lead wire 16 comes through sheathing 14 at the a lead-wire terminal ring 32 and is electrically connected to such ring at a position between ring 32 and sheathing 14. Lead-wire terminal rings 32 are spaced along terminal mount 18 and form an array of lead-wire terminals.

Conductor support 20 holds several pairs of male conductor members 34 in an array. The spacing between adjacent pairs of male conductor members 34 is equal to the spacing between adjacent lead-wire terminal rings 32. Conductor support 20 is a non-conductive substantially rigid member. The male conductor members of each pair of conductor members are electrically joined and lead to an individual wire 36 which may be connected, for example, to electrical sensing and reporting apparatus not shown.

Connector block 22 serves as a convenient disposable means for connecting male conductor members 34 to lead-wire terminal rings 32. Connector block 22 is an integrally formed unitary non-conductive block which has a main surface 38 and first and second ends 40 and 42.

A first elongate cavity or space 44 and an array of second elongate cavities or spaces 46 are formed in connector block 22. First elongate cavity 44 is parallel to main surface 38 and extends the full length of connector block 22. First elongate cavity 44 is complementary to terminal mount 18; that is, first cavity 44 is a generally cylindrical void which receives terminal mount 18. Second elongate cavities 46 each intersect first cavity 44, as illustrated best in FIGS. 3 and 4. Second cavities 46 are complementary to male connector members 34, allowing insertion thereof with a slight degree of freedom.

A pair of second cavities 46 accommodates each pair of male conductor members 34. Each pair of second cavities 46 is spaced from its adjacent pair of second cavities by a distance equal to the spacing between adjacent of lead-wire terminal rings 32 and to the spacing between adjacent pairs of male conductor members 34. Thus, when terminal mount 18 is inserted into first elongate cavity 44, male conductor members 34 may be inserted into second elongate cavities 46 to contact lead-wire terminal rings 32 at each position of insertion of male conductor members.

In use, with terminal mount 18 inserted in first elongate cavity 44, conductor support 20 is brought toward connector block 22 until male conductor members 34 are inserted in second elongate cavities 46. Connector block 22, first cavity 44, second cavities 46, conductor support 20 and its lead-wire terminal rings 32, and male conductor members 34 are configured and arranged such that lead-wire terminal rings 32 and male conductor members 34 are held in engagement by mechanical interference.

More specifically, lead-wire terminal rings 32 have a fixed cross-dimension and male conductor members 34 of each pair are spaced from one another by an amount less than such fixed cross-dimension. By this configuration, such pair of male conductor members 34 are forcibly spread when engaging lead-wire terminal ring 32 therebetween at the intersection of second cavities 46 with first cavity 44. Such spreading causes male conductor members 34 to be biased to a return position such that they squeeze lead-wire terminal ring 32 therebetween to provide firm electrical contact.

As illustrated in FIGS. 5 and 6, an alternative to the one-piece connector block of FIGS. 1-4 is connector block 24 of FIGS. 5 and 6 which is formed of a plurality of sub-blocks 26. Sub-blocks 26 are attached end-to-end by corresponding male and female dovetail connectors on each adjacent pair of sub-blocks 26. Each sub-block 26 forms a portion of a first elongate cavity 44, such portions being aligned. Each sub-block 26 also forms a portion of main surface 38, such portions being co-planar.

Male and female dovetail connectors 48 and 50 have ends 52 and 54, respectively, which form stop means facilitating co-alignment of first elongate cavity portions and co-alignment of the main surface portions when sub-blocks 26 are assembled.

The use of sub-blocks 26 allows connector block 24 to be sized to accommodate any number of lead-wire terminals and individual conductors. The appropriate number of sub-blocks 26 is chosen and they are connected by means of male and female connectors 48 and 50. Then terminal mount 18, regardless of its length and number of terminal rings 32, is inserted into first elongate cavity 44 formed by interconnected sub-blocks 26, and conductor support 20 with a corresponding number of pairs of male conductor members 34 is inserted into second elongate cavities 46 to cause electrical connection of corresponding pairs of terminal rings 32 and male conductor members 34.

Extending from the opposed sidewalls 56 of sub-blocks 26, near the edges thereof farthest from main surfaces 38, are finger-grip protrusions 58. Such protrusions serve to facilitate detachment of connector block 24 from the conductors used therewith, and also aid in detachment of one sub-block from another.

One of the sub-blocks 26 is an end block 60. End block 60 is somewhat longer than the other sub-blocks. End block 60 provides a closed end 64 for first elongate cavity 44 at second end 42 of connector block 24. End block 60 also includes an off-center recess 62 on the connector block main surface 38, shaped like one of second elongate cavities 46. Off-center recess 62 serves to dictate the orientation of conductor support with respect thereto, as explained above.

Using either a one-piece unitary connector block 22 or a connector block 24 formed of sub-blocks 26 greatly facilitates connection of lead wires from tissue-engagement members of brain-contact devices. This substantially shortens the length of a difficult surgical procedure and eliminates any possibility of connection error.

The device of this invention may be made using a variety of readily available parts and materials. Flexible sheet member 28 is preferably a dielectric silicone sheet material such as SILASTIC sheeting, a material available from Dow Chemical Company, Midland, Mich. Tubular sheathing 14 is preferably made of SILASTIC or of a polyurethane member such as TECOFLEX from Thermedics, Inc., Woburn, Mass. A variety of other suitable non-conductive materials may be used for sheathing 14.

A variety of conductive materials may be used for lead-wire terminal rings 32, as would be well known to those skilled in the art. Lead-wires 16 are preferably stainless steel, platinum, or silver strands which are insulated by a teflon coating layer. Connector block 22 and sub-blocks 26 are preferably formed by a molding or machining process using a polysulfone or polycarbonate resin. A particularly preferred material is the polycarbonate resin known as LEXAN, available from General Electric, Schenectady, N.Y.

In certain highly preferred embodiments, blocks 22 and 26 are substantially transparent, as is possible when using, for example, LEXAN. Use of a substantially transparent material allows observation of the engagement of male conductor members 34 with terminal rings 32.

As noted, blocks 22 and sub-blocks 26 are preferably of unitary construction, being entirely free of conductive material, particularly on the walls of cavities 44 and 46. Blocks 22 and 24 are simple devices and are intended to be discarded after use.

Many variations are possible in the devices of this invention. For example, a variety of tissue-engagement members may be used, as noted above, including depth electrodes, strip electrodes and grid electrodes (as shown). Likewise, a variety of conductor supports may be used. Considerable variation is possible in connector block 22 and 24, including variations in shape and variations in the nature of the mating means hold sub-blocks 26 together.

While the principles of this invention have been described in connection with specific embodiments, it should be understood clearly that these descriptions are made only by way of example and are not intended to limit the scope of the invention.

I claim:

1. In an electrical connection device of the type for connecting a plurality of lead wires with individual conductors, the improvement comprising:

the lead wires extending to a terminal mount and to an array of lead-wire terminals on and forming a part of the terminal mount;

a conductor support holding the individual conductors in a conductor array; and a connector block having a first space and an array of second spaces each intersecting the first space, the first space receiving the terminal mount and the array of second spaces receiving the conductor array, the connector block, terminal mount and conductor array configured and arranged such that the lead-wire terminals and individual conductors are held in engagement by mechanical interference.

2. The electrical connection device of claim 1 wherein:

the terminal mount is an elongate member having the lead-wire terminals spaced therealong;

the first space is a first elongate cavity in the connector block shaped to receive the elongate member, said first elongate cavity being defined by a cavity surface formed of non-conductive material, said cavity surface contacting the elongate member received in said cavity;

the individual conductors are male members protruding from the conductor support; and the second spaces are second elongate cavities in the connector block shaped to receive the male members, said second spaces each being defined by a second-space surface formed of non-conductive material, said second-space surfaces contacting the male members received in said second spaces.

3. The electrical connection device of claim 2 further including means biasing the male members and lead-wire terminals together at the intersections of the second elongate cavities with the first elongate cavity.

4. The electrical connection device of claim 3 wherein:

the lead-wire terminals have substantially fixed cross-dimensions;

the connector block has a pair of adjacent second elongate cavities corresponding to each lead-wire terminal; and each individual conductor includes a pair of said male members in the pair of second elongate cavities, said pair of male members spaced from one another by an amount less than the fixed cross-dimension, whereby the pair of male members are forcibly spread in engaging the lead-wire terminals therebetween to provide said biasing means.

5. The electrical connection device of claim 2 wherein the connector block is substantially transparent, whereby engagement of the conductors with the lead-wire terminals is visible.

6. The electrical connection device of claim 2 wherein the connector block is of non-conductive one-piece construction.

7. The electrical connection device of claim 2 wherein the connector block includes a main surface extending substantially parallel to the first elongate cavity, said second elongate cavities extending from the main surface to the first elongate cavity.

8. The electrical connection device of claim 7 further including an off-center recess on the connector block main surface to dictate orientation of the conductor support with respect thereto.

9. The electrical connector device of claim 7 wherein the connector block has opposed sidewalls extending to opposite edges of the main surface and finger-grip protrusions on the opposed sidewalls for facilitating detachment of the connector block.

10. The electrical connection device of claim 7 wherein:

the connector block is formed of a plurality of sub-blocks attached end-to-end, said sub-blocks having mating means on each adjacent pair of sub-blocks securing to one another the sub-blocks of each such pair;

the sub-blocks each forming a portion of the first elongate cavity and a portion of the main surface and having a subset of the second elongate cavities, whereby the connector block can be sized to accommodate varying numbers of lead-wire terminals and conductors by choosing the number of sub-blocks to be attached to one another.

11. The electrical connection device of claim 10 wherein the mating means include stop means facilitating co-alignment of the first elongate cavity portions and co-alignment of the main surface portions.

12. The electrical connection device of claim 11 wherein the mating means are corresponding male and female dove-tail connectors.

13. In an electrical brain-contact device of the type having a tissue-engagement member with a plurality of electrodes, separate leadwires from the tissue-engagement member for each electrode, and means away from the tissue-engagement member to connect the lead wires with individual conductors, the improvement comprising:

the lead wires extending from the tissue-engagement member to a terminal mount and to an array of lead-wire terminals on and forming a part of the terminal mount;

a conductor support holding the individual conductors in a conductor array; and a connector block having a first space and an array of second spaces each intersecting the first space, the first space receiving the terminal mount and the array of second spaces receiving the conductor array, the connector block, terminal mount and conductor array configured and arranged such that the lead-wire terminals and individual conductors are held in engagement by mechanical interference, whereby electrical connection of a brain-contact device is facilitated.

14. The electrical connection device of claim 13 wherein:

the terminal mount is an elongate member including a sheathing with the lead wires therein and rings around the sheathing spaced therealong to form the lead-wire terminals;

the first space is a first elongate cavity in the connector block shaped to receive the elongate member, said first elongate cavity being defined by a cavity surface formed of non-conductive material, said cavity surface contacting the elongate member received in said cavity;

the individual conductors are male members protruding from the conductor support; and the second spaces are second elongate cavities in the connector block shaped to receive the male members, said second spaces each being defined by a second-space surface formed of non-conductive material, said second-space surfaces contacting the male members received in said second spaces.

15. The electrical connection device of claim 14 further including means biasing the male members and lead-wire terminals together at the intersections of the second elongate cavities with the first elongate cavity.

16. The electrical connection device of claim 15 wherein:

the lead-wire terminals have substantially fixed cross-dimensions;

the connector block has a pair of adjacent second elongate cavities corresponding to each lead-wire terminal; and each individual conductor includes a pair of said male members in the pair of second elongate cavities, said pair of male members spaced from one another by an amount less than the fixed cross-dimension, whereby the pair of male members are forcibly spread in engaging the lead-wire terminals therebetween to provide said biasing means.

17. The electrical connection device of claim 14 wherein the connector block is substantially transparent, whereby engagement of the conductors with the lead-wire terminals is visible.

18. The electrical connection device of claim 14 wherein the connector block is of non-conductive one-piece construction.

19. The electrical connection device of claim 14 wherein the connector block includes a main surface extending substantially parallel to the first elongate cavity, said second elongate cavities extending from the main surface to the first elongate cavity.

20. The electrical connection device of claim 19 further including an off-center recess on the connector block main surface to dictate orientation of the conductor support with respect thereto.

21. The electrical connector device of claim 19 wherein the connector block has opposed sidewalls extending to opposite edges of the main surface and finger-grip protrusions on the opposed sidewalls for facilitating detachment of the connector block.

22. The electrical connection device of claim 19 wherein:

the connector block is formed of a plurality of sub-blocks attached end-to-end, said sub-blocks having mating means on each adjacent pair of sub-blocks securing to one another the sub-blocks of each such pair;

the sub-blocks each forming a portion of the first elongate cavity and a portion of the main surface and having a subset of the second elongate cavities, whereby the connector block can be sized to accommodate varying numbers of lead-wire terminals and conductors by choosing the number of sub-blocks to be attached to one another.

23. The electrical connection device of claim 22 wherein the mating means include stop means facilitating co-alignment of the first elongate cavity portions and co-alignment of the main surface portions.

24. The electrical connection device of claim 23 wherein the mating means are corresponding male and female dove-tail connectors.

* * * * *